United States Patent [19]

Stoev et al.

[11] 4,090,937
[45] May 23, 1978

[54] ELECTROPHORETIC TECHNIQUE FOR VARYING THE CONCENTRATION OF A COLLOIDAL SOLUTION

[75] Inventors: Stoycho Mitrev Stoev; Yordan Vladimirov Vuchev; Lyubomir Vladimirov Kuzev; Georgi Petrov Atzinov, all of Sofia, Bulgaria

[73] Assignee: Vish Minno-Geoloshki Institute, Sofia, Bulgaria

[21] Appl. No.: 709,396

[22] Filed: Jul. 28, 1976

[51] Int. Cl.[2] .............................................. B01D 13/02
[52] U.S. Cl. .......................... 204/180 R; 204/299 R; 204/300 R
[58] Field of Search ................... 204/180 R, 299, 186, 204/300; 210/DIG. 18, DIG. 22; 208/187; 209/127 B; 128/32

[56] References Cited

U.S. PATENT DOCUMENTS

| 894,070 | 7/1908 | Schwerin | 204/180 R |
|---|---|---|---|
| 2,740,756 | 4/1956 | Thomas | 204/180 R |
| 3,205,160 | 9/1965 | Stenzel et al. | 204/180 R X |
| 3,412,002 | 11/1968 | Hubby | 204/180 R |
| 3,432,426 | 3/1969 | Megel | 208/187 |
| 3,468,778 | 9/1969 | Hirs et al. | 204/180 R |
| 3,642,605 | 2/1972 | Chenel et al. | 204/300 |
| 3,773,648 | 11/1973 | Welzen et al. | 204/299 |
| 3,799,863 | 3/1974 | Zeineh | 204/299 |
| 3,821,102 | 6/1974 | Fletcher et al. | 204/180 R X |
| 3,847,785 | 11/1974 | Allington | 204/299 |

*Primary Examiner*—Arthur C. Prescott

[57] ABSTRACT

The processing speed and efficiency of separation of a first phase of a colloidal suspension by an electrophoretic technique is described. The medium to be concentrated is introduced into a funnel on the top of an enclosure whose bottom wall carries a first, vertically extending electrode, the solution flowing generally downwardly from the funnel along guide paths that are separately defined between the opposed walls of the first electrode and the peripheries of a pair of rotationally mounted drum electrodes situated on opposite sides of the first electrode. The first electrode is vibrated during the downward flow of the fluid while an electric field is applied across the separate guide paths, thereby efficiently separating the first phase of the solution. The remaining product adheres to the periphery of each of the rotating second and third electrodes, such product being removed therefrom by baffle plates supported in the tank and coupled to suitable discharge chutes. The baffle plates are positioned above a second pair of discharge chutes which are carried on the bottom wall of the tank for receiving the separated first phase at the bottom of the guide paths.

4 Claims, 1 Drawing Figure

U.S. Patent
May 23, 1978
4,090,937
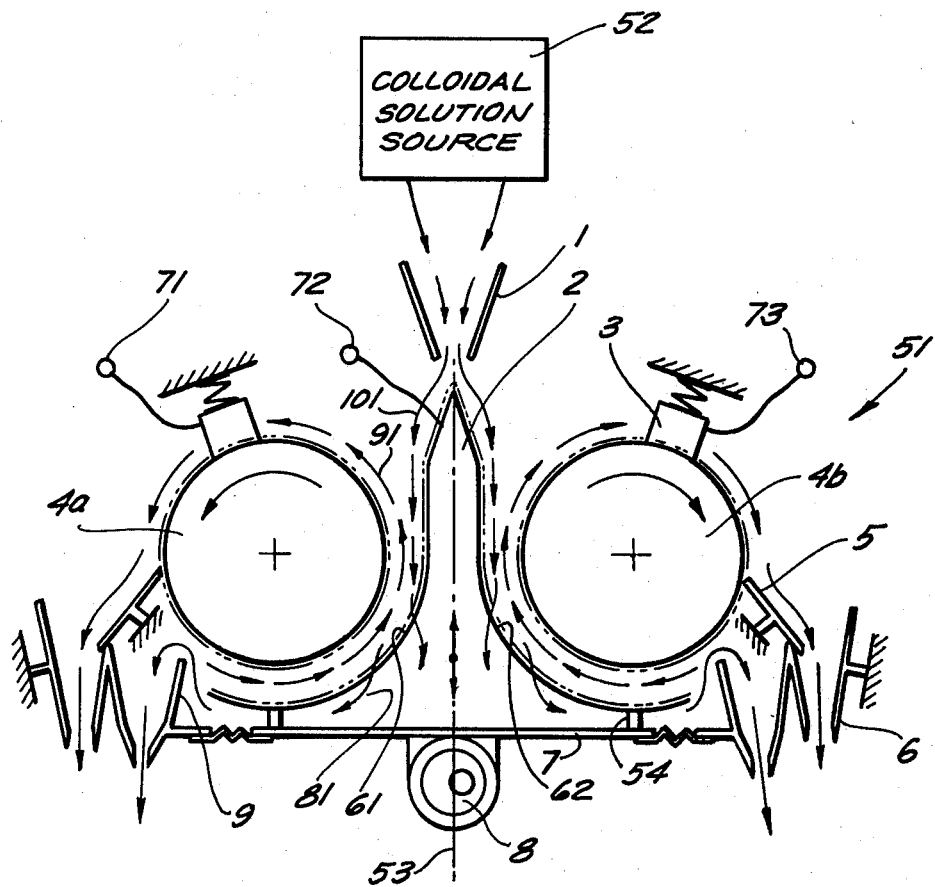

ELECTROPHORETIC TECHNIQUE FOR VARYING THE CONCENTRATION OF A COLLOIDAL SOLUTION

BACKGROUND OF THE INVENTION

The invention relates to methods of and apparatus for electrophoretically varying the concentration of a colloidal solution by separating therefrom an electrically-influenceable first phase, which phase is generally present in the solution in the form of fine particles. Such techniques are exemplified, e.g., in U.S. Pat. No. 3,847,785 issued to W. B. Allington on Nov. 12, 1974; U.S. Pat. No. 3,799,863 issued to R. A. Zeinah on Mar. 26, 1974; U.S. Pat. No. 3,773,648 issued to Welzen et al on Nov. 20, 1973; and U.S. Pat. No. 3,821,102 issued to J. C. Fletcher on June 28, 1974.

In known techniques of this type, the first phase to be separated is removed from the solution by applying an electric field across a guide path through which the solution to be concentrated is passed. Up to now, this procedure has not exhibited a high selectivity of separation of the desired first phase from the colloidal particles of the solution, despite a relatively high expenditure of electrical energy for applying the field across the guide paths. In addition, even the relatively inefficient separation of the first phase has been slow.

SUMMARY OF THE INVENTION

The present invention solves the above-mentioned disadvantages by providing an improved technique for electrophoretic concentration of a colloidal solution having an electrically-influenceable first phase. Illustratively, the concentration is carried out in an enclosure having a bottom wall from which an elongated first electrode extends in a vertical direction, such first electrode being associated with a surrounding pair of drum-type second and third electrodes which are mounted for rotation in a vertical plane.

The space between the opposed vertical surfaces of the first electrode and the periphery of the associated one of the second and third electrodes are employed as separate fluid-guiding paths for the suspension to be concentrated. For this purpose, a funnel is disposed above the top edge of the first electrode, such funnel receiving the solution to be concentrated and directing such fluid into separate flows along the first and second paths.

An electric field is applied between the first electrode and individual ones of the second and third electrodes to apply an electric field across the first and second paths while the solution flows downwardly therethrough. Simultaneously, the first electrode is oscillated by a vibrator which is attached to the bottom wall of the enclosure, such vibratory motion imparted to the solution serving to increase both the speed and the efficiency of the separation of the first phase.

The separated first phase is discharged from the enclosure by means of a pair of chutes supported in the bottom of the enclosure below the first and second paths. The concentrate remaining in the solution adheres, as a colloidal product, to the periphery of the rotating drum electrodes, and is separately separated therefrom by means of a pair of baffle plates that are disposed radially outwardly of the drum electrodes in the enclosure and which extend toward the outer peripheries thereof. The baffle plates, which are situated above the openings of the chutes in the bottom wall of the tank, guide the removed concentrate to a separate set of chutes for discharging such concentrate from the enclosure.

BRIEF DESCRIPTION OF THE DRAWING

The invention is further set forth in the following detailed description taken in conjunction with the appended drawing, in which the single FIGURE is a representation of an arrangement for carrying out an electrophoretic concentration technique in accordance with the invention.

DETAILED DESCRIPTION

Referring now to the drawing, the numeral 51 diagrammatically represents an enclosure for carrying out an electrophoretic technique in accordance with the invention for separating a finely-divided, electrically-influenceable first phase from a colloidal solution introduced into the enclosure 51 from a suitable source 52.

The enclosure has a bottom wall 7, from which an elongated first electrode 2 extends upwardly along an axis 53 of the enclosure, the bottom end of the electrode being curved outwardly and downwardly to engage a pair of supports 54, 54 on the bottom surface 7. The opposed walls of the electrode 2 may be made permeable to the phase of the solution to be separated, to allow a flow of such first phase along the bottom surface 7 to be discharged from the enclosure 51 in the manner described below.

A pair of drum-type electrodes 4a and 4b are individually supported for rotation in the enclosure 51 on opposite sides of the electrode 2. The axes of rotation of the drum electrodes are horizontal, whereby such drums may be rotated in opposite directions as shown in a vertical plane by suitable drive means (not shown).

The space between the outer periphery of the drum 4a and the adjacent wall of the electrode 2 defines a first fluid-guiding path 61, such path extending generally downwardly toward the bottom of the enclosure 51. In like manner, the space between the periphery of the drum 4b and the adjacent wall of the electrode 2 defines a second fluid-guiding path 62, which is symmetrical to the path 61. Suitable facilities are associated with the enclosure 51 for providing an electric field across the paths 61 and 62 while the solution to be concentrated is flowed downwardly therealong. Specifically, a pair of spring-loaded brushes 3—3 are urged against the peripheries of the respective drums 4a and 4b from suitable fixed points of the enclosure. A suitable power source (not shown) is coupled to respective terminals 71, 72 and 73 of the brushes 3 and the electrode 2, with the resulting voltage across the electrodes 71 and 72 being effective to provide the required electric field across the path 61, while the voltage across the electrodes 72 and 73 is effective to provide the required electric field across the path 62.

In order to direct a colloidal solution from the source 52 into the parallel paths 61 and 62 within the enclosure 51, a funnel 1 is disposed in the upper portion of the enclosure in overlying relation to a pointed upper end of the electrode 2. Such funnel 1 receives the solution from the source 52, and directs it around the upper end of the electrode 2 and down along the parallel paths 61 and 62.

A vibrator 8 is associated with the bottom surface 7 of the enclosure to impart an oscillatory motion to the electrode 2 and thereby to the fluid streaming down along the paths 61 and 62. The application of such vibration has been found to greatly decrease the time necessary to separate the first phase from the solution during the application of the electric field to the solution flowing in the paths, and such vibratory motion has simultaneously been found to minimize the consumption of electrical energy for obtaining a given degree of separation of the first phase. Simultaneously, it has been found that the combined electrical and vibratory excitation of the colloidal solution improves the selectivity of the arrangement in the separation and isolation of the particles of the various substances of the suspension.

When the combined vibratory and electrical excitation is applied to the fluid in the paths 61 and 62, the first phase separated thereby permeates through the wall of the electrode 2, and flows along the bottom wall surface 7 of the enclosure as shown by arrows 81. A pair of discharge chutes 9, 9 are associated with the bottom wall 7 for collecting and discharging the separated first phase from the enclosure.

In order to accommodate the enriched concentrated solution left after the first phase is separated therefrom, the drum electrodes 4a and 4b are rotated in opposition to the downward flow of the solution from the funnel 1, such latter flow being represented by arrows 101. With this technique, the concentrate adheres to the outer periphery of the respective electrodes 4a and 4b, and are received and collected by a pair of baffle plates 5, 5 which are individually supported in the enclosure 51 on radially outer sides of the drum electrodes. The baffle plates extend upwardly and obliquely toward the periphery of the rotating electrodes 4a and 4b, thereby to intercept the concentrate adhered to the periphery of the drums and to guide the collected concentrate into a pair of discharge chutes 6, 6 supported in the enclosure 51.

In order to prevent intermixing, with the concentrate, of the separated flow of the first phase via the chutes 9, the baffle plates 5 are positioned over the upper top ends of the chutes 6 in the manner depicted in the drawing.

Without in any way limiting the generality of the foregoing, the following examples of vibro-electrophoretic treatment in accordance with the invention are given for purposes of illustration:

EXAMPLE 1

Pulp in the form of a kaolin concentrate containing about 32.4% $Al_2O_3$ was introduced into the arrangement of the drawing from the source 52 and subjected to the above-mentioned vibro-electrophoretic treatment in a single operation, and with a current density of about 0.1 $A/m^2$ to charge the concentrate. The pulp was subjected to a vibration sufficient to remove differences in temperature and density within the pulp and to prevent movements of the first phase to the drum electrodes. The first phase, in the form of superfine sand, remained uncharged by the electrical excitations and was thereby separated from the charged concentrate to a degree sufficient to increase the concentration of $Al_2O_3$ in the final product to 36.8%.

EXAMPLE 2

Pulp in the form of a kaolin concentrate containing 12.25% $Al_2O_3$ was subjected to a one-pass vibro-electrophoretic treatment in the manner set forth in Example 1, and was enriched thereby to a 35.3% concentration of $Al_2O_3$.

In the foregoing, an illustrative apparatus and technique for carrying out the invention has been described. Many variations and modifications will now occur to those skilled in the art. It is accordingly desired that the scope of the appended claims not be limited to the specific disclosure herein contained.

What is claimed is:

1. In a method for electrophoretically varying the concentration of a colloidal solution by displacement of an electrically-influenceable phase thereof, the method comprising the step of passing the solution through a prescribed path while subjecting the said phase to an electric field to separate the said phase from the remaining concentrate of the solution, the improvement comprising the step of continuously imparting a vibratory motion to the solution along the prescribed path during the application of the electric field.

2. A method according to claim 1, wherein the prescribed path is defined by an enclosure extending along a vertical axis and having a bottom wall, a first elongated electrode secured within the enclosure and extending upwardly from the bottom wall along the vertical axis, second and third drum electrodes individually mounted in the enclosure for rotation about horizontal axes, the second and third electrodes being respectively disposed on opposite sides of the first electrode, the peripheries of the respective second and third electrodes being disposed adjacent to and spaced from the opposed vertically extending walls of the first electrode to individually define first and second fluid-guiding paths therebetween extending generally downwardly toward the bottom wall of the enclosure, means associated with the first, second, and third electrodes for applying an electric field across the first and second paths to effect a separation of the said phase from the solution when the solution is flowed downwardly along the first and second paths, and directing means centrally disposed above and in communication with the upper end of the first electrode for dividing the medium into separate flows along the first and second paths, first and second collection means individually disposed below the first and second paths and supported on the bottom wall of the enclosure for discharging the said separated phase, and wherein the first electrode is vibrated to impart said vibratory motion to the solution along its prescribed path during the application of the electric field.

3. A method according to claim 2, wherein said prescribed path is further defined by first and second baffle plates individually supported in the enclosure outwardly of the second and third electrodes and extending toward the peripheries of the respective electrodes to receive the colloidal product adhering to the periphery of such electrodes after the said phase is separated from the solution, and third and fourth collection means individually supported in the enclosure and associated with the first and second baffle plates for discharging from the enclosure the colloidal product received by the respective baffle plates.

4. A method according to claim 3, wherein the first and second baffle plates are individually disposed above the first and second collection means for isolating the discharge of the said phase.

* * * * *